(12) United States Patent
Sato (10) Patent No.: US 9,646,223 B2
(45) Date of Patent: May 9, 2017

(54) IMAGE MEASURING METHOD, SYSTEM, DEVICE, AND PROGRAM

(71) Applicant: NEC Corporation, Minato-ku, Tokyo (JP)

(72) Inventor: Akari Sato, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/652,886

(22) PCT Filed: Dec. 3, 2013

(86) PCT No.: PCT/JP2013/007079
§ 371 (c)(1),
(2) Date: Jun. 17, 2015

(87) PCT Pub. No.: WO2014/103181
PCT Pub. Date: Jul. 3, 2014

(65) Prior Publication Data
US 2015/0339540 A1    Nov. 26, 2015

(30) Foreign Application Priority Data
Dec. 26, 2012  (JP) ................................ 2012-282056

(51) Int. Cl.
*G06K 9/60* (2006.01)
*G01N 33/00* (2006.01)
(Continued)

(52) U.S. Cl.
CPC ............. *G06K 9/60* (2013.01); *G01N 21/251* (2013.01); *G01N 21/27* (2013.01);
(Continued)

(58) Field of Classification Search
CPC .... G06K 9/4652; G06K 9/60; G06K 2209/17; G06T 7/0042; G06T 7/0044;
(Continued)

(56) References Cited

U.S. PATENT DOCUMENTS 6,366,681 B1 * 4/2002 Hutchins ....................... 382/110
2005/0022264 A1 * 1/2005 Fanger ........................... 800/282
(Continued)

FOREIGN PATENT DOCUMENTS

CN   102269576 A   12/2011
CN   102706293 A   10/2012
(Continued)

OTHER PUBLICATIONS

International Search Report for PCT Application No. PCT/JP2013/007079, mailed on Mar. 11, 2014.
(Continued)

*Primary Examiner* — Andrew W Johns (57) ABSTRACT

An image measuring system includes: a reflecting body arranged near a plant to be measured; a photographing unit for photographing the reflecting body and outputting the photographed image; an image analyzing unit for detecting, in the photographed image, the area of the reflecting body and acquiring the color information of the area; an absolute spectral irradiance distribution calculating unit for calculating, on the basis of the color information, the absolute spectral irradiance distribution, which is the distribution of the absolute values of the spectral irradiance in the area; a photon flux density calculating unit for calculating, on the basis of the absolute spectral irradiance distribution, the photon flux density; and a Leaf Area Index calculating unit for calculating, on the basis of the photon flux density, the Leaf Area Index.

10 Claims, 6 Drawing Sheets

(51) Int. Cl.
*G01N 21/27* (2006.01)
*G01N 21/47* (2006.01)
*G01N 21/25* (2006.01)
*G01N 21/84* (2006.01)

(52) U.S. Cl.
CPC ......... *G01N 21/4738* (2013.01); *G01N 21/84* (2013.01); *G01N 33/0098* (2013.01); *G01N 2021/8466* (2013.01); *G01N 2201/12* (2013.01)

(58) Field of Classification Search
CPC G06T 2207/10024; G06T 2207/30188; G01N 21/25; G01N 21/251; G01N 21/27; G01N 21/4738; G01N 2021/8466; G01N 33/0098
See application file for complete search history.

(56) References Cited

U.S. PATENT DOCUMENTS

2013/0182911 A1* 7/2013 Tsukada ............... G06K 9/60 382/110
2013/0276368 A1* 10/2013 Takayama et al. .... G01N 21/64 47/58.1 R

FOREIGN PATENT DOCUMENTS

| JP | 2007-171033 A | 7/2007 |
|---|---|---|
| JP | 2008-111725 A | 5/2008 |
| JP | 2011-133451 A | 7/2011 |
| WO | 2012/073507 A1 | 6/2012 |
| WO | 2012/073519 A1 | 6/2012 |
| WO | 2012/073520 A1 | 6/2012 |

OTHER PUBLICATIONS

H. W. Jensen, "Photon Mapping", Ohmsha, Ltd., Jul. 2002, p. 29, 32.

D. Judd, D. L. MacAdam and G. Wyszecki, "Spectral Distribution of Typical Daylight as a Function of Correlated Color Temperature", Journal of the Optical Society of America, vol. 54, No. 8, Aug. 1964, pp. 1031-1040, English Abstract.

E. Kaneko, M. Toda, H. Aoki and M. Tsukada, "Daylight Spectrum Model under Weather Conditions from Clear Sky to Cloudy", Proc. of IEEE 21st International Conference on Pattern Recognition, 2012, English Abstract, English Abstract.

Monsi and Saeki, "On the Factor Light in Plant Communities and its Importance for Matter Production," Annals of Botany 95, 2005, pp. 549-567, Originally published as : Japanese Journal of Botany 14, Mar. 1953, pp. 22-52.

Masatoshi Aoki and other three persons "Remote Sensing of Chlorophyll Content of Leaf (II), Effective Spectral Reflection Characteristics for Evaluations of Chlorophyll Content and Leaf Area Index of Plant Community, Environment Control in Biology", 1986, vol. 24, 1st issue, pp. 33-39, English Summary in the last part.

"The characteristics in light climate of plant populations in coastal agroforestry in China", Peng Fangren et al., 2002 vol. 21, No. 1, Feb. 25, 2002, pp. 11-15. URL: http://www.ecolsci.com/EN/volumn/volumn_1193.shtml.

"Determination of Land and Ocean Reflective, Radiative, and Biophysical Properties Using Multiangle Imaging", J.V. Martonchik et al., IEEE Transactions on Geoscience and Remote Sensing, vol. 36 Issue: 4, Jul. 31, 1998, pp. 1266-1281.

Chinese Office Action for CN Application No. 201380068174.5 mailed on Sep. 21, 2016 with English Translation.

* cited by examiner

IMAGE MEASURING METHOD, SYSTEM, DEVICE, AND PROGRAM

This application is a National Stage Entry of PCT/JP2013/007079 filed on Dec. 3, 2013, which claims priority from Japanese Patent Application 2012-282056 filed on Dec. 26, 2012, the contents of all of which are incorporated herein by reference, in their entirety.

TECHNICAL FIELD

The present invention relates to an image measuring method, an image measuring system, an image measuring device and an image measuring program to measure a leaf area index.

BACKGROUND ART

The leaf area index (hereinafter, called as LAI) represents the sum of areas of leaves that overlap in a certain direction (e.g. in a vertical direction) per unit area in a plant community or the like in croplands or in forests. The LAI is used as an index to grasp plant growth or cultivation condition in greenhouse cultivation or the like.

As a method for measuring the LAI, for instance, there is proposed an indirect measuring method using an illuminance sensor. In this method, for instance, illuminances are measured in an upper region and in a lower region within a plant community to estimate the LAI based on the measured illuminances thereof.

Further, as a related technique, PTL 1 describes a method, in which reflectors arranged in a plant community are photographed, and illuminances are calculated based on color information of the reflectors to estimate the LAI.

Furthermore, PTL 2 describes the LAI indirect measuring method. In the method described in PTL 2, an indirect measuring system photographs an image of a predetermined area with respect to each of near infrared light and red light, using a wide angle lens and an electronic element. Then, the indirect measuring system obtains a luminance value with respect to each of the near infrared light and the red light in each of segment areas obtained by dividing the predetermined area. Then, the indirect measuring system obtains a ratio of luminance values between the near infrared light and the red light in each of the detail areas, estimates a relative amount of solar radiation based on the ratio of luminance values, and obtains the leaf area index based on the relative amount of solar radiation.

CITATION LIST

Patent Literature

[PTL 1] International Patent Publication No. 2012/073519
[PTL 2] Japanese Laid-open Patent Publication No. 2007-171033

Non Patent Literature

[NPL1] H. W. Jensen, "Photon Mapping", Ohmsha, Ltd. p 29, 32
[NPL2] D. Judd, D. L. MacAdam and G. Wyszecki, "Spectral Distribution of Typical Daylight as a Function of Correlated Color Temperature", Journal of the Optical Society of America, vol. 54, No. 8, August, 1964, pp. 1031-1040
[NPL3] E. Kaneko, M. Toda, H. Aoki and M. Tsukada, "Daylight Spectrum Model under Weather Conditions from Clear Sky to Cloudy", Proc. of IEEE 21st International Conference on Pattern Recognition, 2012.
[NPL4] Monsi and Saeki, "On the Factor Light in Plant Communities and its Importance for Matter Production," Annals of Botany 95, 2005, pp. 549-567, Originally published as: Japanese Journal of Botany 14, March, 1953, pp. 22-52

SUMMARY OF INVENTION

Technical Problem

In the method of PTL 1, the illuminance is utilized as an intensity of light for calculating the LAI. However, since a correlation between the illuminance and the LAI is low, precision of the calculated LAI is low.

Further, in the method of PTL 2, the LAI is calculated based on the ratio of the luminance values between the near infrared light and the red light by the indirect measuring system in which the measuring direction is restricted. Even when using the luminance value, however, precision in calculating the LAI is low, and furthermore, the measuring direction may be restricted with respect to sunlight, which is a light source.

In view of the above, an object of the present invention is to provide an image measuring method, an image measuring system, an image measuring device and an image measuring program, which are capable of precisely calculating the LAI.

Solution to Problem

An image measuring method in the present invention includes:
  photographing a reflector arranged in vicinity of a plant to be measured, and outputting a photographed image of the reflector;
  detecting an area where the reflector is photographed within the photographed image;
  acquiring color information of the area;
  calculating an absolute spectral irradiance distribution of the area based on the color information, the absolute spectral irradiance distribution being a distribution of absolute values of spectral irradiances in the area;
  calculating a photosynthetic photon flux density based on the absolute spectral irradiance distribution; and
  calculating a leaf area index based on the photosynthetic photon flux density.

An image measuring system in the present invention includes:
  a reflector arranged in vicinity of a plant to be measured;
  a photographing unit that photographs the reflector and outputting a photographed image of the reflector;
  an image analysis unit that detects an area where the reflector is photographed within the photographed image and acquiring color information of the area;
  an absolute spectral irradiance distribution calculating unit that calculates an absolute spectral irradiance distribution based on the color information, the absolute spectral irradiance distribution being a distribution of absolute values of spectral irradiances in the area;
  a photosynthetic photon flux density calculating unit that calculates a photosynthetic photon flux density based on the absolute spectral irradiance distribution; and
  a leaf area index calculating unit that calculates a leaf area index based on the photosynthetic photon flux density.

An image measuring device in the present invention uses in an image measuring system provided with a reflector arranged in vicinity of a plant to be measured, and a photographing unit that photographs the reflector and outputting a photographed image of the reflector, the image measuring device includes:

an image analysis unit that detects an area where the reflector is photographed within the photographed image and acquiring color information of the area;

an absolute spectral irradiance distribution calculating unit that calculates an absolute spectral irradiance distribution based on the color information, the absolute spectral irradiance distribution being a distribution of absolute values of spectral irradiances in the area;

a photosynthetic photon flux density calculating unit that calculates a photosynthetic photon flux density based on the absolute spectral irradiance distribution; and a leaf area index calculating unit that calculates a leaf area index based on the photosynthetic photon flux density.

In the present invention, a non-transitory computer readable recording medium that stores a computer program to use in an image measuring system provided with a reflector arranged in vicinity of a plant to be measured, and a photographing unit that photographs the reflector and outputting a photographed image of the reflector, the program causing a computer to execute:

an image analysis processing of detecting an area where the reflector is photographed within the photographed image and acquiring color information of the area;

an absolute spectral irradiance distribution calculation processing of calculating an absolute spectral irradiance distribution based on the color information, the absolute spectral irradiance distribution being a distribution of absolute values of spectral irradiances in the area;

a photosynthetic photon flux density calculation processing of calculating a photosynthetic photon flux density based on the absolute spectral irradiance distribution; and a leaf area index calculation processing of calculating a leaf area index based on the photosynthetic photon flux density.

Advantageous Effects of Invention

According to the present invention, it is possible to precisely calculate the LAI.

DESCRIPTION OF EMBODIMENTS

In the following, an exemplary embodiment of the present invention is described referring to the drawings.

Figure 1:
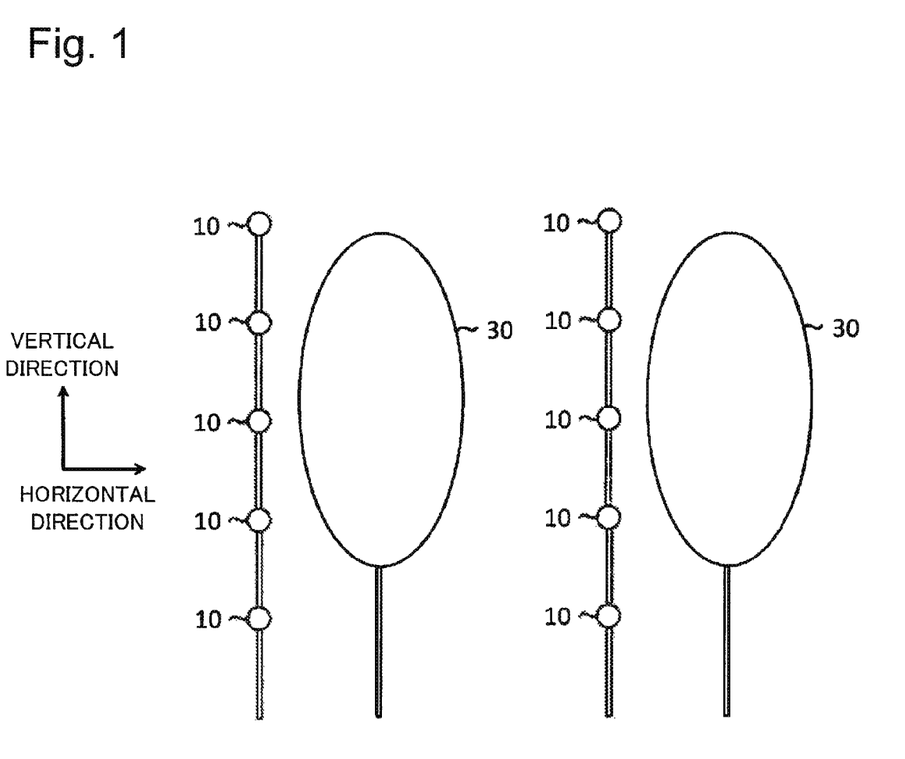
FIG. 1 is a front view of a measurement system using the LAI image measuring system, viewing from the front side with respect to plant communities, according to the present invention.
Figure 2:
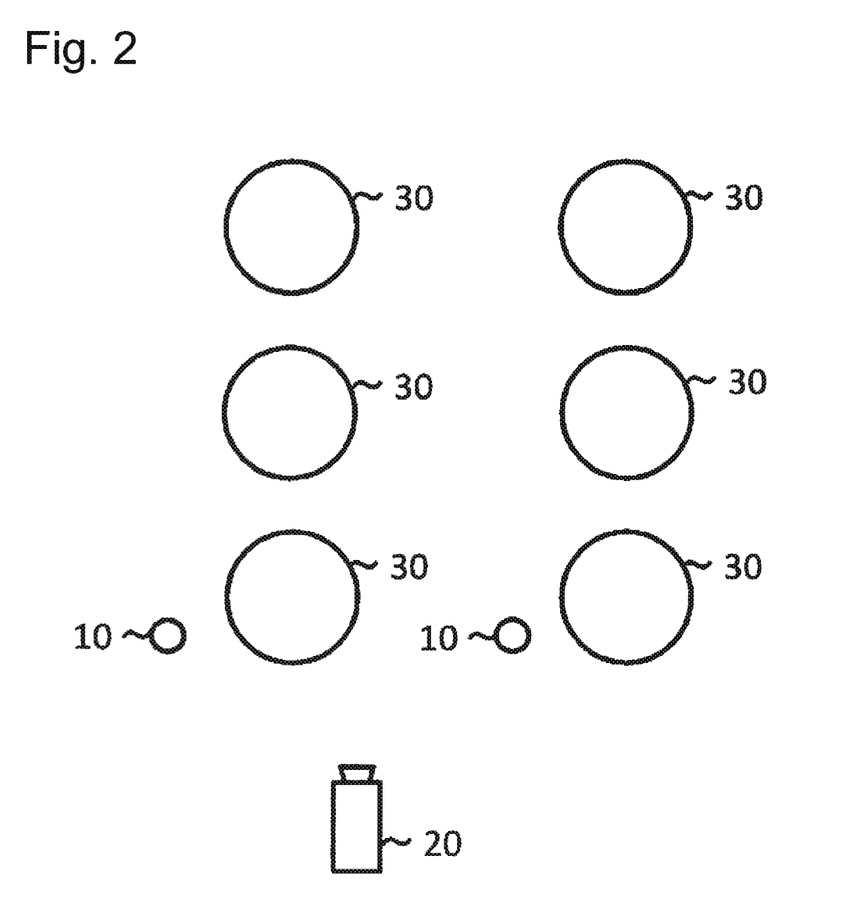
FIG. 2 is a top plan view of the measurement system using the LAI image measuring system, viewing from the upper surface side with respect to the plant communities.

FIG. 1 is a front view of a measurement system using the LAI image measuring system (leaf area index image measuring system), viewing from the front side with respect to plant communities, according to the present invention. In the FIG. 1, plant communities 30 are illustrated with a sectional state taken along a plane. FIG. 2 is a top plan view of the measurement system using the LAI image measuring system, viewing from the upper surface side with respect to the plant communities. As illustrated in FIG. 1, in the present exemplary embodiment, "a vertical direction" indicates a direction perpendicular to the ground, and "a horizontal direction" indicates a direction horizontal to the ground.

As illustrated in FIG. 1, to simplify the description, it is assumed that the plant communities 30 according to the present exemplary embodiment are a group of plants for crops planted in a row. Further, as illustrated in FIG. 2, the plant communities 30 are a group of plants planted in two rows in the depth direction (a direction toward the depth side from the front side in FIG. 1, hereinafter, may be called as a longitudinal direction). Alternatively, the plant communities 30 may be the group of plants of one row or a group of plants of more than two rows.

In the present exemplary embodiment, an example is described, in which the LAI image measuring system is applied for measuring the LAI of plant communities for the crops (e.g. tomatoes or cucumbers) in croplands such as fields or plastic greenhouses. The invention, however, is not limited to the present exemplary embodiment, and for instance, the LAI image measuring system may be used for measuring the LAI of a group of trees in the forests.

As illustrated in FIG. 1 and FIG. 2, a group of arrayed reflectors 10 in which a plurality of reflectors 10 are arrayed in the vertical direction are arranged in the vicinity of each plant community 30. Further, as illustrated in FIG. 2, a camera 20 is arranged at a position capable of photographing the reflectors 10 without being blocked by the plant communities 30. In this example, as illustrated in FIG. 2, the camera 20 is arranged on the front side of the reflectors 10. The camera 20 is arranged at such a position that there is no obstacle such as leaves between each of the reflectors 10 and the camera 20, which may block the reflectors 10.

In the example illustrated in FIG. 1 in the present exemplary embodiment, five reflectors 10 are arranged in the vertical direction with respect to each plant community 30. Therefore, ten reflectors 10 in total are arranged in a vertical direction. However, the number of reflectors 10 which can be arranged is not limited to the example in the present exemplary embodiment. For instance, it is also possible to arrange twelve or more reflectors 10 (six or more reflectors 10 are arranged in the vertical direction with respect to each plant community 30).

Specifically, the reflector 10 is implemented by a spherical body, whose surface has perfect diffusion (Lambertian) reflectance characteristics, and whose color information (reflectance) is known. For instance, the reflector 10 may also be one of polyhedral structures of various types, or a flat reflection plate.

The reflector 10 in the present exemplary embodiment has a perfect white color (reflectance p=10). Further, as far as the color (reflectance p) of the reflector 10 is known, the color of the reflector 10 is not limited to a perfect white color, but may be red, gray, yellow, or orange. However, the color of the reflector 10 is preferably at least a color other than green in order to discriminate the reflector 10 from the plants in the plant communities 30.

Further, each reflector 10 has a property such that the intensity of reflected light from the reflectors 10 arranged in an upper region is large, and the intensity of reflected light from the reflectors 10 arranged in a lower region is small due to the shadows generated by the plant communities 30, in view of a fact that the reflectors 10 are arranged in the vicinity of the plant communities 30. This makes it possible to measure the LAI in the vertical direction by measuring the intensities of light reflected from the plurality of reflectors 10 arranged away from one another in the vertical direction, and comparing the intensities of light to each other, and grasp a degree of overlapping of leaves in the plant communities 30, viewing from the vertical direction. The vicinity of the plant communities 30 is within a predetermined distance from the plant communities 30 (e.g. within 50 cm). The reflectors 10 are each arranged away from one another in the vertical direction so that the intensities of light reflected on the each reflector 10 are appropriately varied.

Specifically, the camera 20 is implemented by a photographing device such as a digital camera capable of photographing a color image. As long as the camera 20 is capable of photographing a color image, the camera 20 is not limited to a camera for photographing a still image, but, for instance, may be a video camera capable of photographing a moving image. Further, the camera 20 photographs the reflectors 10, and outputs photographed images of the reflectors 10 to an LAI image measuring device 40 (not illustrated in FIG. 1 and FIG. 2) to be described later.

In the present exemplary embodiment, the reflectors 10 irradiated with sunlight are photographed for measuring the LAI in the vertical direction so that it is desirable to arrange the camera 20 at a position capable of photographing an upper hemisphere of each reflector 10, which is a spherical body (e.g. at a position higher than all the reflectors 10 in a vertical direction).

Further, FIG. 1 illustrates an example of measuring, in which five reflectors 10 are arranged in the vertical direction at a position in the vicinity of each plant community 30. Alternatively, five each of reflectors 10 may also be arranged away from one another in the vertical direction at a predetermined interval (e.g. at an interval of 50 cm) in the longitudinal direction of each plant community 30 (in other words, the reflectors 10 are arranged in a lattice manner, viewing from the side in the longitudinal direction) for measurement. The aforementioned modification also makes it possible to measure a distribution state of the LAI in the longitudinal direction of the plant communities 30.

Figure 3:
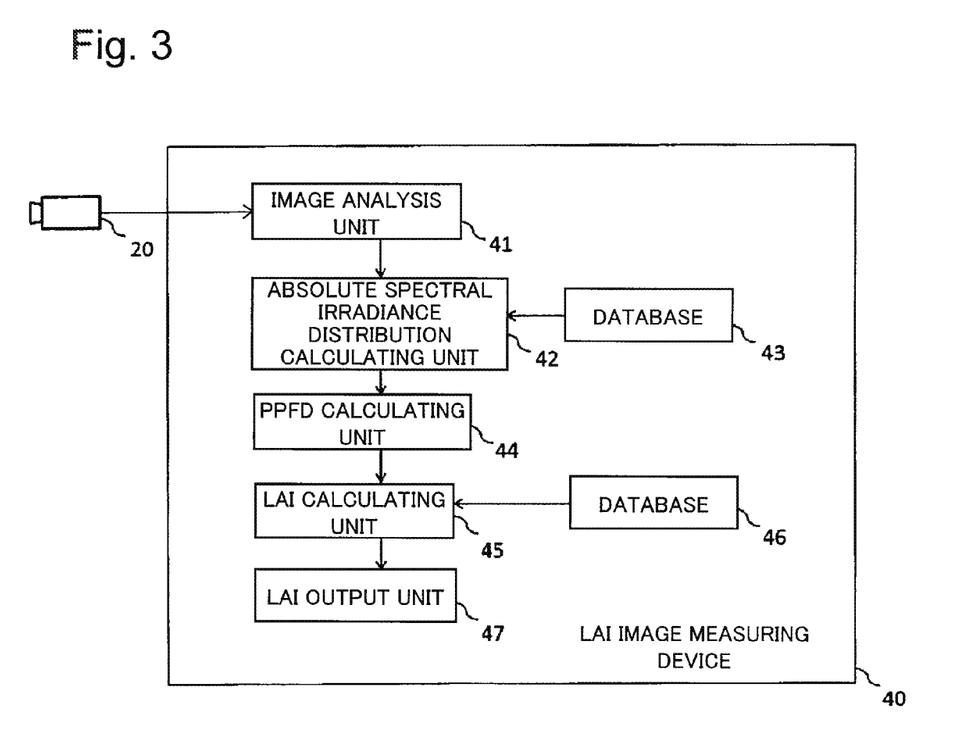
FIG. 3 is a block diagram illustrating an example of a configuration of the LAI image measuring system according to the present invention.

FIG. 3 is a block diagram illustrating an example of a configuration of the LAI image measuring system. As illustrated in FIG. 3, the LAI image measuring system includes the camera 20 photographing the reflectors 10 illustrated in FIG. 2, and the LAI image measuring device 40.

As illustrated in FIG. 3, the LAI image measuring device 40 includes an image analysis unit 41, an absolute spectral irradiance distribution calculating unit 42, a database 43, a PPFD (Photosynthetic photon flux density) calculating unit 44, a LAI (leaf area index) calculating unit 45, a database 46, and a LAI output unit 47. Further, as illustrated in FIG. 3, a photographed image to be output from the camera 20 is output to the LAI image measuring device 40. Specifically, the LAI image measuring device 40 is implemented by an information processing device such as a personal computer which is operated according to a program.

Specifically, the image analysis unit 41 is implemented by a CPU of an information processing device which is operated according to a program. The image analysis unit 41 calculates a tristimulus value XYZ (hereinafter, called as an XYZ value) of a photographed image input from the camera 20.

The image analysis unit 41 specifies (detects) an area where each reflector 10 is photographed within the photographed image, based on the known color information or known shape information of the reflector 10, and obtains a luminance value in the specified area. Specifically, the image analysis unit 41 specifies an area where a white object is photographed within the photographed image, and extracts a partial image of being the specified area. In the present exemplary embodiment, a plurality of white reflectors 10 are arranged so that the image analysis unit 41 specifies a plurality of areas, and extracts partial images of being the respective specified areas. Then, the image analysis unit 41 calculates the XYZ value of each of the extracted partial images.

In the following, an example of a method for calculating the XYZ value of an object (reflector 10) within the color image photographed by the camera 20 is described. First of all, the image analysis unit 41 detects an area where the object is photographed, using color information and shape information of the input photographed image. Subsequently, the image analysis unit 41 acquires color information RGB in the detected area of the object, and calculates the tristimulus value XYZ based on the acquired color information RGB.

In the following, regarding the color information RGB of the image photographed by the color image input device 20, it is assumed that a chrominance of RGB phosphor of the device and a chrominance of white are designated in advance as color characteristics of the color image input device, and the color information RGB is uniquely converted to the tristimulus value XYZ. In the following, an example of a conversion method thereof is described. The relationship between the color information RGB of the input image and the tristimulus value XYZ is expressed by following Eqn. (1).

[Math 1]

$$\begin{pmatrix} X \\ Y \\ Z \end{pmatrix} = M_{3 \times 3} \begin{pmatrix} R \\ G \\ B \end{pmatrix} \quad (1)$$

In Eqn. (1), $M_{3 \times 3}$ is a 3×3 conversion matrix. Further, it is assumed that the color information RGB has linear characteristics without gamma correction. The conversion equation may be such that it is possible to uniquely convert the color information RGB to the tristimulus value XYZ. For instance, the conversion may be expressed by following Eqn. (2).

[Math 2]

$$\begin{pmatrix} X \\ Y \\ Z \end{pmatrix} = M_{3\times 9} \begin{pmatrix} R \\ G \\ B \\ R^2 \\ G^2 \\ B^2 \\ R*G \\ G*B \\ B*R \end{pmatrix} \quad (2)$$

In Eqn. (2), $M_{3\times 9}$ is a 3×9 conversion matrix.

It is possible to calculate one or both of $M_{3\times 3}$ and $M_{3\times 9}$ in advance by performing color calibration of the color image input device, using a known color patch.

The absolute spectral irradiance distribution calculating unit 42 calculates an absolute spectral irradiance distribution, which is a distribution of absolute values of spectral irradiances in the area of the reflector 10 within the photographed image. In the following example, the absolute spectral irradiance distribution calculating unit 42 calculates an absolute irradiance, utilizing that the reflector 10 is an object having Lambertian reflectance characteristics, and whose reflectance ρ is known.

It is assumed that I and R are respectively irradiance and radiance at a certain point on an object surface having Lambertian reflectance characteristics, and ρ is a reflectance of the object. In case that a bi-directional reflectance distribution function (BRDF) is expressed by $f_{BRDF}$, as described in NPL 1, $f_{BRDF}$ is expressed by following Eqn. (3).

[Math 3]

$$f_{BRDF} = \frac{R}{I} \quad (3)$$

Further, as described in NPL 1, $f_{BRDF}$ of the object surface having Lambertian reflectance characteristics is expressed by following Eqn. (4).

[Math 4]

$$f_{BRDF} = \frac{\rho}{\pi} \quad (4)$$

In the example of the present exemplary embodiment, the reflector 10 has a perfect white color so that following Eqn. (5) is obtained by setting p=1.0 in Eqn. (4).

[Math 5]

$$f_{BRDF} = \frac{1}{\pi} \quad (5)$$

The absolute spectral irradiance distribution calculating unit 42 converts a tristimulus value Y (luminance value Y) calculated based on the Eqn. (1) or Eqn. (2) into an absolute radiance R (unit: W/m²/sr) at each pixel position within the image of the reflector 10 depending on light irradiated from the reflector 10 toward the camera, by obtaining information on the aperture value F, the shutter speed, and the gain of a camera lens at the time of photographing.

In this case, for instance, there is prepared a table in advance, in which the aperture value F, the shutter speed, the luminance value Y and the absolute radiance are associated with one another. In response to input of the aperture value F, the shutter speed and the obtained luminance value Y, the absolute spectral irradiance distribution calculating unit 42 extracts the associated absolute radiance R from the aforementioned table by utilizing the table. Alternatively, the absolute spectral irradiance distribution calculating unit 42 may further perform computation such as interpolation with respect to the extracted value.

Further, the surface of the reflector 10 has Lambertian reflectance characteristics so that the absolute radiance R is converted to the absolute irradiance I by using Eqn. (3) and Eqn. (5).

Alternatively, the absolute spectral irradiance distribution calculating unit 42 may directly calculate an absolute irradiance from a table. In this case, there is prepared a table in advance, in which an aperture value F, a shutter speed, a luminance value Y, and an absolute irradiance are associated with one another. The absolute spectral irradiance distribution calculating unit 42 extracts, from the table, an absolute irradiance I associated with an aperture value F, a shutter speed, and an obtained luminance value Y. Further alternatively, the absolute spectral irradiance distribution calculating unit 42 may also perform interpolation or the like with respect to an extracted value.

Further alternatively, the absolute spectral irradiance distribution calculating unit 42 may also calculate the absolute irradiance, using a conversion equation, without using the table. In this case, there is expressed the conversion equation in advance, in which the aperture value F, the shutter speed, the luminance value Y and the absolute radiance or the absolute irradiance are associated with one another. Then, the absolute spectral irradiance distribution calculating unit 42 may convert the aperture value F, the shutter speed and the obtained luminance value Y into the absolute radiance or into the absolute irradiance by using the conversion equation.

Figure 4:
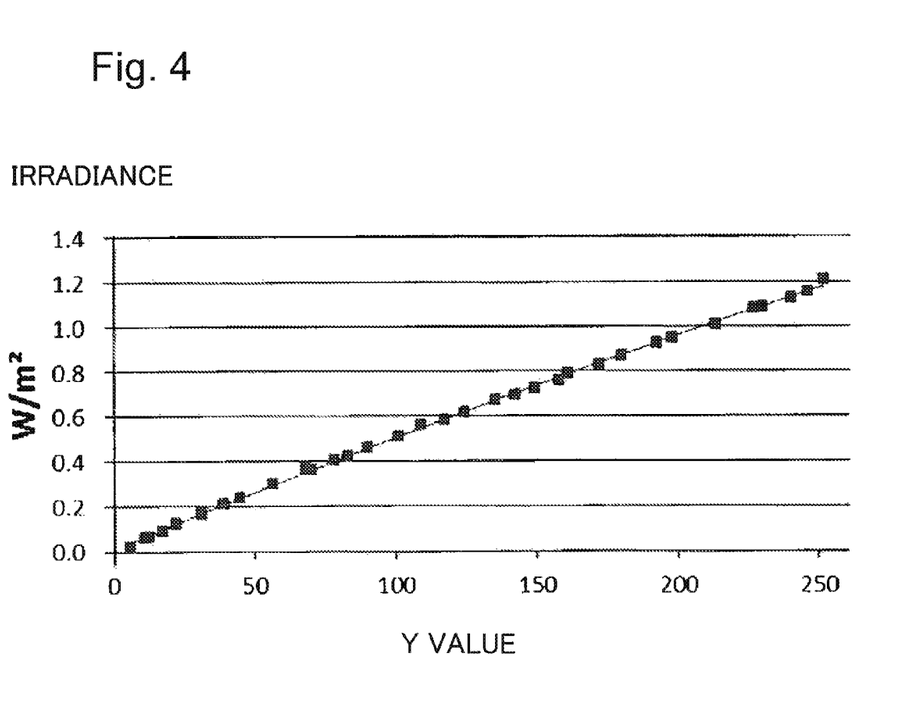
FIG. 4 is a graph, in which an example of a relationship between a luminance value Y and irradiance is plotted.

FIG. 4 is a graph illustrating a relationship between the luminance value Y and the irradiance, in case that the aperture value F, the shutter speed and the gain are set to a fixed value. As is clear from FIG. 4, an approximate conversion equation can be easily calculated by using these values.

Next, the absolute spectral irradiance distribution calculating unit 42 calculates each chrominance x, y based on the tristimulus value XYZ, using Eqn. (6).

[Math 6]

$$x = \frac{X}{X+Y+Z}, y = \frac{Y}{X+Y+Z} \quad (6)$$

Next, the absolute spectral irradiance distribution calculating unit 42 obtains a spectral distribution (a relative spectral radiance distribution) of radiances of light irradiated from an object surface toward the camera, using the chrominance x, y.

In the following, as an example of a method for calculating the relative spectral radiance distribution based on the chrominance x, y, a case using the CIE daylight model described in NPL 2 is described. As illustrated in following Eqn. (7), the absolute spectral irradiance distribution calculating unit 42 calculates $M_1$ and $M_2$, using the chrominance x, y.

[Math 7]

$$M_1 = \frac{-1.3515 - 1.7703x + 5.9114y}{0.0241 + 0.2562x - 0.7341y}, \qquad (7)$$

$$M_2 = \frac{-0.0300 - 31.4424x + 30.0717y}{0.0241 + 0.2562x - 0.7341y}$$

When it is assumed that λ is the wavelength of light to be irradiated, as illustrated in Eqn. (8), the relative spectral radiance distribution R(λ) (the vector R(λ) (with tilde) in Eqn. (8)) is obtained by using an average vector $S_0(\lambda)$, a first main component vector $S_1(\lambda)$ and a second main component vector $S_2(\lambda)$ of CIE daylight given by NPL 2.

[Math 8]

$$\tilde{R}(\lambda) = S_0(\lambda) M_1 S_1(\lambda) + M_4 S_2(\lambda) \qquad (8)$$

The relative spectral radiance distribution R(λ) is a relative distribution, when it is assumed that R(λ) is 1 when λ=560.

The surface of the reflector 10 has Lambertian reflectance characteristics so that the relative spectral radiance distribution R(λ) obtained in this example is equal to a relative spectral irradiance distribution Ir(λ).

In this example, the absolute spectral irradiance distribution calculating unit 42 calculates the relative spectral irradiance distribution, using the CIE daylight model. However, it is not limited to this example and, for instance, the Bird model or the like described in NPL 3 may be used.

Next, the absolute spectral irradiance distribution calculating unit 42 calculates an absolute spectral irradiance distribution I(λ) based on the obtained absolute irradiance I and the obtained relative spectral irradiance distribution Ir(λ). Specifically, the absolute spectral irradiance distribution calculating unit 42 calculates the absolute spectral irradiance distribution I(λ) by multiplying a value of the relative spectral irradiance distribution Ir(λ) at each wavelength with an constant, using the absolute irradiance I. For instance, the constant is set to such a value that the integrated value of the relative spectral irradiance distribution Ir(λ) in the wavelength range of from 400 nm to 700 nm is equal to the absolute irradiance I. Then, the absolute spectral irradiance distribution calculating unit 42 calculates the absolute spectral irradiance distribution I(λ) by multiplying the value of the relative spectral irradiance distribution Ir(λ) at each wavelength with the constant.

Specifically, the database 43 is implemented by a storage device such as a magnetic disk device or an optical disc device. In the present exemplary embodiment, the database 43 stores the conversion table to use in converting the aperture value F, the shutter speed and the luminance value Y into the absolute radiance or into the absolute irradiance. Specifically, the conversion table to be stored in the database 43 includes the aperture value F, the shutter speed and the luminance value Y in association with the absolute radiance or with the absolute irradiance. For instance, the conversion table to be stored in the database 43 is configured by setting in advance the absolute radiance or the absolute irradiance measured by a dedicated device, and the luminance value Y obtained based on the aperture value F, a shutter speed and the photographed image under a condition of several sample cases.

The PPFD calculating unit 44 calculates an intensity of light to be utilized for photosynthesis (photosynthetic photon flux density) based on the obtained absolute spectral irradiance distribution I(λ).

In the following, as an example of a method for calculating the light intensity (photosynthetic photon flux density) by the PPFD calculating unit 44, a method of calculating a photosynthetic effective photon flux density is expressed. The photosynthetic photon flux density is a mass (unit: μmol/m²/s) of photons of light in the wavelength range of from 400 nm to 700 nm per unit time and unit area. The following relationship is established with respect to the irradiance by definition of the photosynthetic photon flux density.

[Math 9]

energy per unit time and unit area(irradiance,W/m²)

=energy per photon(J/photon)×number of photons passing per unit time and unit area(number of photons/m²/s)

=energy per photon(J/photon)×mass of photons passing per unit time and unit area(mol/m²/s)× Avogadro's number(number/mol)

=energy per photon(J/photon)×(mass of photons passing per unit time and unit area(mol/m²/s)× 10⁶)×Avogadro's number(number/mol)×10⁻⁶

=energy per photon(J/photon)×photosynthetic photon flux density (μmol/m²/s)×Avogadro's number (number/mol)×10⁻⁶ (9)

The energy per photon (J/photon) is expressed by hc/λ, where λ is a wavelength, h is a Planck's constant and c is a light velocity. Following Eqn. (10) is established using hc/λ and Eqn. (9).

[Math 10]

$$I(\lambda) = \left(\frac{hc}{\lambda}\right) \times P(\lambda) \times N_A \times 10^{-6} \qquad (10)$$

In Eqn. (10), each symbol has the following meaning.

I(λ): irradiance of light at wavelength λ

P(λ): photosynthetic photon flux density of light at wavelength λ

P: photosynthetic photon flux density (in the wavelength range of from 400 nm to 700 nm)

Following Eqn. (11) is yielded by modifying Eqn. (10).

[Math 11]

$$P(\lambda) = 10^6 \frac{I(\lambda)\lambda}{hcN_A} \qquad (11)$$

Further, the photosynthetic photon flux density P, as expressed by following Eqn. (12), is obtained by integrating P(λ) yielded by Eqn. (11) in the wavelength range of from 400 nm to 700 nm.

[Math 12]

$$P = 10^6 \int_{400}^{700} \frac{I(\lambda)}{hcN_A} d\lambda \qquad (12)$$

The LAI calculating unit 45 calculates the LAI (leaf area index) based on the obtained photosynthetic photon flux density (PPFD). A photosynthetic photon flux density $P_i$ of the reflector 10 at the height i is compared with a photosynthetic photon flux density $P_0$ of the reflector 10 at a reference position for calculating the LAI (the LAI in this case is expressed as $F_i$) of leaves in the upper region above the height i. In this example, the reference position of the reflector 10 is a position of the reflector 10 mounted at the uppermost position, in other words, the position substantially free of an influence such as shadows generated by the leaves between the reflector 10 and the sun, where it is possible to obtain a reference photosynthetic photon flux density.

In the present exemplary embodiment, the LAI calculating unit 45 obtains the LAI at the height i by extracting, from the LAI conversion table stored in the database 46, the LAI associated with a difference between the PPFD of the reflector 10 at the height i, which is calculated by the PPFD calculating unit 44, and the PPFD of the reflector 10 at the reference position.

Alternatively, the LAI calculating unit 45 may also obtain the LAI by performing a computation processing using Eqn. (13) described in NPL 4.

[Math 13]

$$P_i/P_0 = e^{-KF_i} \qquad (13)$$

In Eqn. (13), K represents an absorption coefficient, whose value differs depending on each plant, and even in the same plant, differs depending on an external factor such as weather or a time zone. Further, F represents an integrated leaf area index, in other words, the LAI.

The database 46 stores the LAI conversion table to use in converting the photosynthetic photon flux density into the LAI. Specifically, in the LAI conversion table stored in the database 46, the photosynthetic photon flux density and the LAI are associated with each other. The LAI conversion table stored in the database 46 is, for instance, configured by setting in advance the photosynthetic photon flux density measured with use of a generally used photon sensor, and the LAI obtained at the measurement time under a condition of several sample cases.

The LAI output unit 47 displays the LAI calculated by the LAI calculating unit 45 on a computer display or a like device.

Figure 5:
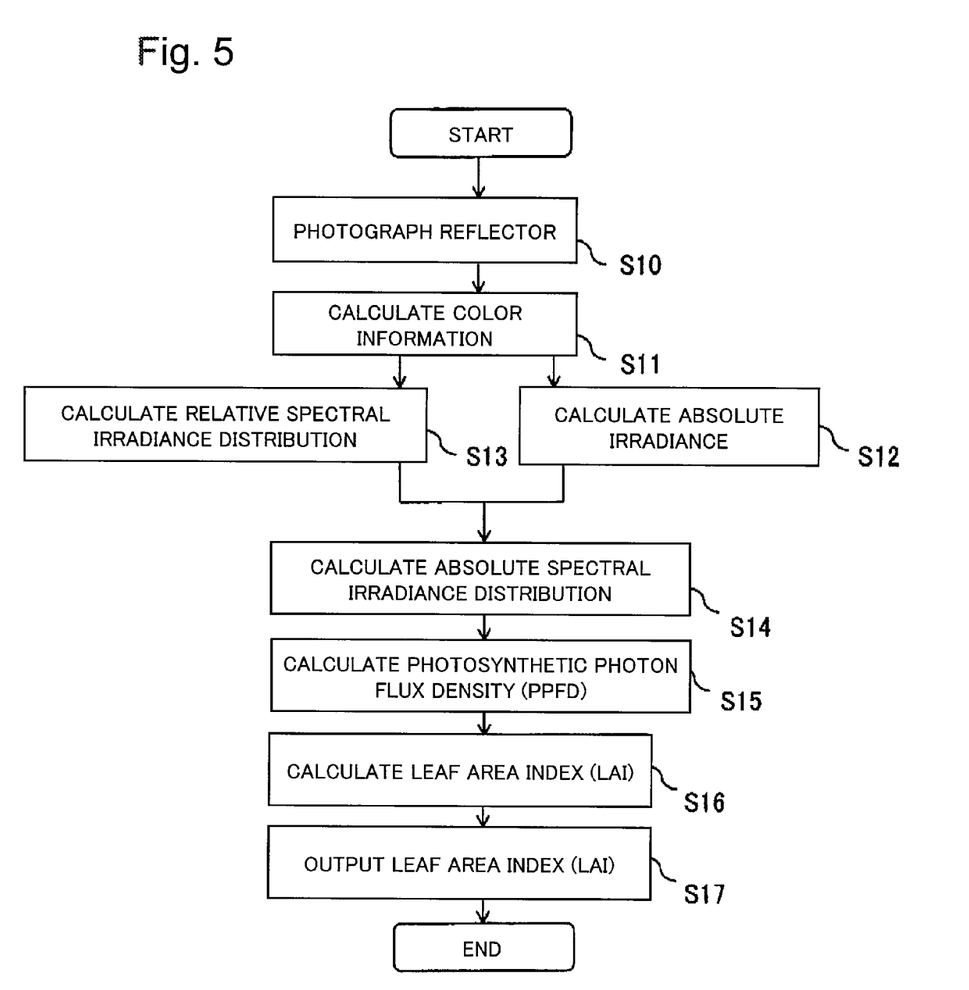
FIG. 5 is a flowchart illustrating an example of an operation of calculating the LAI, using the LAI image measuring system according to the present invention.

Next, an operation to be performed by the LAI image measuring system is described. FIG. 5 is a flowchart illustrating an example of an operation of measuring the LAI by the LAI image measuring system. In the present exemplary embodiment, as illustrated in FIG. 1 and FIG. 2, the camera 20 is arranged at the position capable of photographing the reflector 10 without being blocked by the plant communities 30.

First of all, the camera 20 photographs an image in the direction in which the reflector 10 is arranged (Step S10). The LAI image measuring device 40 receives the photographed image from the camera 20.

The LAI image measuring device 40, for instance, acquires the color information (in the present exemplary embodiment, white color) of the reflector 10, which is stored in advance in a storage device (not illustrated), specifies the area where a white object is photographed within the photographed image received from the camera 20, and extracts a partial image of being the specified area. In the present exemplary embodiment, a plurality of white reflectors 10 are arranged so that the image analysis unit 41 specifies plural areas and extracts partial images of being the respective specified areas. Then, the LAI image measuring device 40 calculates color information of the each extracted partial images (Step S11). Specifically, the image analysis unit 41 acquires color information RGB of the area where the object is photographed, and calculates the tristimulus value XYZ based on the the acquired color information RGB.

Further, the LAI image measuring device 40 calculates the absolute irradiance, which is the absolute value of the irradiance based on the calculated luminance value Y (Step S12). In the present exemplary embodiment, the LAI image measuring device 40 acquires from the irradiance conversion table stored in the database, the irradiance associated with the calculated luminance value Y, the aperture value F and the shutter speed obtained at the time of photographing. Alternatively, the LAI image measuring device 40 may calculate the irradiance associated with the calculated Y value, the aperture value and the shutter speed obtained at the time of photographing, from the conversion equation using the predetermined luminance value Y, the predetermined aperture value F and the predetermined shutter speed.

Furthermore, the LAI image measuring device 40 calculates the chrominance xy value based on the calculated tristimulus value XYZ and calculates the relative spectral irradiance distribution (Step S13). In the present exemplary embodiment, the LAI image measuring device 40 calculates the relative spectral irradiance distribution from the chrominance xy value, using the CIE daylight model.

Next, the LAI image measuring device 40 calculates the absolute spectral irradiance distribution, based on the the absolute value of the calculated irradiance and the relative spectral irradiance distribution (Step S14). In the present exemplary embodiment, the LAI image measuring device 40 sets the constant to such a value that the integrated value of the spectral irradiance distribution in the wavelength range of from 400 nm to 700 nm is equal to the calculated absolute irradiance, and obtains the absolute spectral irradiance distribution by multiplying the relative spectral irradiance distribution with the constant.

Next, the LAI image measuring device 40 calculates the photosynthetic photon flux density (PPFD) based on the calculated absolute spectral irradiance distribution (Step S15).

Next, the LAI image measuring device 40 calculates the leaf area index (LAI) based on the calculated PPFD (Step S16). In the present exemplary embodiment, the LAI image measuring device 40 calculates the LAI by extracting, from the LAI conversion table, the LAI associated with the difference between the calculated upper and lower values of PPFD. Alternatively, the LAI image measuring device 40 may also calculate the LAI according to Eqn. (13), using the calculated PPFD.

After calculation of the LAI is finished, the LAI image measuring device 40 displays the calculated LAI on a display or the like (Step S17).

The LAI image measuring system in the present exemplary embodiment calculates the photosynthetic photon flux density having a high correlation to the LAI, and calculates the LAI based on the photosynthetic photon flux density, and so makes it possible to more precisely calculate the LAI.

Figure 6:
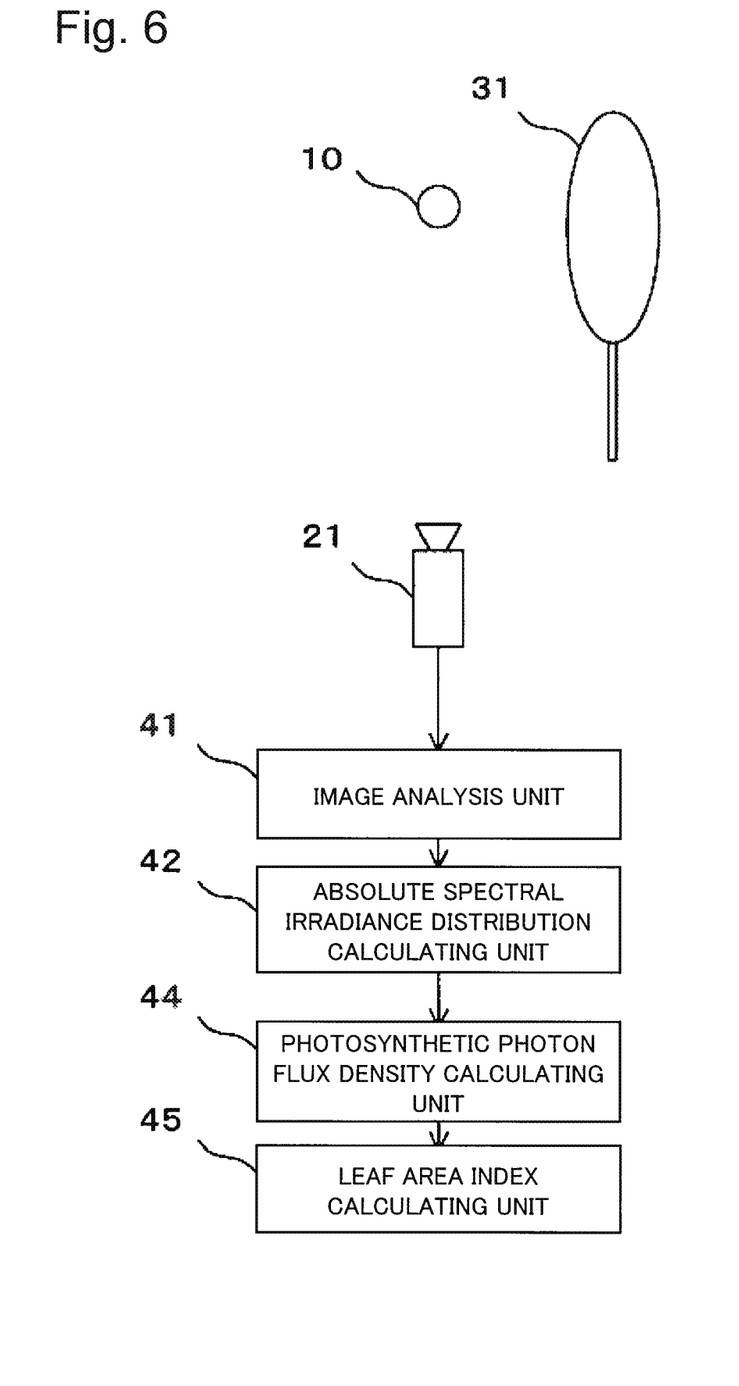
FIG. 6 is a block diagram illustrating a main configuration of the LAI image measuring system according to the present invention.

FIG. 6 is a block diagram illustrating a main configuration of an image measuring system according to the present invention. As illustrated in FIG. 6, the image measuring system according to the present invention is provided with, as main components, a reflector 10 arranged in the vicinity of a plant 31 to be measured; the photographing unit 21 which photographs the reflector 10, and outputs a photographed image of the reflector 10; the image analysis unit 41 which detects the area where the reflector 10 is photographed within the photographed image, and acquires the color information of the area; the absolute spectral irradiance distribution calculating unit 42 which calculates the absolute spectral irradiance distribution based on the color information, the absolute spectral irradiance distribution being a distribution of the absolute values of the spectral irradiances in the area; the photosynthetic photon flux density calculating unit 44 which calculates the photosynthetic photon flux density based on the absolute spectral irradiance distribution; and the leaf area index calculating unit 45 which calculates the leaf area index based on the photosynthetic photon flux density.

Further, in the exemplary embodiment mentioned above, image measuring systems and image measuring devices as described in the following sections (1) to (5) are also disclosed.

(1) An image measuring system (e.g. a LAI image measuring system) provided with a reflector (e.g. the reflector 10) arranged in vicinity of a plant to be measured (e.g. a part of the plants of the plant communities 30); a photographing unit (e.g. the camera 20) which photographs the reflector and outputs a photographed image of the reflector; an image analysis unit (e.g. the image analysis unit 41) which detects an area of the reflector within the photographed image and acquires color information of the area; an absolute spectral irradiance distribution calculating unit (e.g. the absolute spectral irradiance distribution calculating unit 42) which calculates an absolute spectral irradiance distribution, based on the color information, the absolute spectral irradiance distribution being a distribution of absolute values of spectral irradiances in the area; a photosynthetic photon flux density calculating unit (e.g. the PPFD calculating unit 44) which calculates a photosynthetic photon flux density based on the absolute spectral irradiance distribution; and a leaf area index calculating unit (e.g. the LAI calculating unit 45) which calculates a leaf area index based on the photosynthetic photon flux density.

(2) The image measuring system may be configured such that the reflector includes a perfect diffusion reflection surface, whose color is known.

(3) The image measuring system may be configured to be provided with a storage unit (e.g. the database 46) which stores the photosynthetic photon flux density and the leaf area index in association with each other, and may be configured such that the leaf area index calculating unit extracts the leaf area index associated with the calculated photosynthetic photon flux density from the storage unit to calculate the leaf area index.

(4) The image measuring system may be configured such that the absolute spectral irradiance distribution calculating unit calculates a tristimulus value including a luminance value in the area based on the color information, calculates an absolute irradiance based on the luminance value, the absolute irradiance being an absolute value of an irradiance in the area, calculates a chrominance in the area based on the tristimulus value, calculates a relative spectral irradiance distribution based on the chrominance, the relative spectral irradiance distribution being a relative distribution of spectral irradiances in the area, and calculates an absolute spectral irradiance distribution based on the absolute irradiance and the relative spectral irradiance distribution.

(5) An image measuring device (e.g. the LAI image measuring device 40) to use in an image measuring system provided with a reflector (e.g. the reflector 10) arranged in vicinity of a plant to be measured (e.g. a part of the plants of the plant communities 30); and a photographing unit (e.g. the camera 20) which photographs the reflector and outputs a photographed image of the reflector, wherein the image measuring device is provided with an image analysis unit (e.g. the image analysis unit 41) which detects an area where the reflector is photographed within the photographed image and acquires color information of the area; an absolute spectral irradiance distribution calculating unit (e.g. the absolute spectral irradiance distribution calculating unit 42) which calculates an absolute spectral irradiance distribution based on the color information, the absolute spectral irradiance distribution being a distribution of absolute values of spectral irradiances in the area; a photosynthetic photon flux density calculating unit (e.g. the PPFD calculating unit 44) which calculates a photosynthetic photon flux density based on the absolute spectral irradiance distribution; and a leaf area index calculating unit (e.g. the LAI calculating unit 45) which calculates a leaf area index based on the photosynthetic photon flux density.

This application is based upon and claims the benefit of priority from Japanese patent application No. 2012-2820256, filed on Dec. 26, 2012, the disclosure of which is incorporated herein in its entirety by reference.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

INDUSTRIAL APPLICABILITY

The present invention is applicable for use in grasping the plant growth or the cultivation condition in greenhouse cultivation or the like.

REFERENCE SIGNS LIST

10 Reflector
20 Camera
21 Photographing unit
30 Plant community
31 Plant
40 LAI image measuring device
41 Image analysis unit
42 Absolute spectral irradiance distribution calculating unit
43, 46 Database
44 Photosynthetic photon flux density (PPFD) calculating unit
45 Leaf area index (LAI) calculating unit

What is claimed is:
1. An image measuring method comprising:
photographing a reflector arranged in vicinity of a plant to be measured, and outputting a photographed image of the reflector;
detecting an area where the reflector is photographed within the photographed image;
acquiring color information of the area;

calculating an absolute spectral irradiance distribution of the area based on the color information, the absolute spectral irradiance distribution being a distribution of absolute values of spectral irradiances in the area;

calculating a photosynthetic photon flux density based on the absolute spectral irradiance distribution; and calculating a leaf area index based on the photosynthetic photon flux density.

2. The image measuring method according to claim 1, wherein the reflector includes a perfect diffusion reflection surface whose color is known.

3. The image measuring method according to claim 1, further comprising:

storing the photosynthetic photon flux density and the leaf area index in association with each other; and extracting the leaf area index in association with the calculated photosynthetic photon flux density for calculating the leaf area index.

4. The image measuring method according to claim 1, further comprising:

calculating a tristimulus value including a luminance value in the area based on the color information;

calculating an absolute irradiance based on the luminance value, the absolute irradiance being an absolute value of an irradiance of light in the area;

calculating a chrominance in the area based on the tristimulus value;

calculating a relative spectral irradiance distribution based on the chrominance, the relative spectral irradiance distribution being a relative distribution of spectral irradiances in the area; and calculating the absolute spectral irradiance distribution based on the absolute irradiance and the relative spectral irradiance distribution.

5. An image measuring system, comprising:

a reflector arranged in vicinity of a plant to be measured;

an image capturing device that photographs the reflector and outputs a photographed image of the reflector;

a processor; and memory storing executable instructions that, when executed by the processor, causes the processor to perform as:

an image analysis unit that detects an area where the reflector is photographed within the photographed image and acquires color information of the area;

an absolute spectral irradiance distribution calculating unit that calculates an absolute spectral irradiance distribution based on the color information, the absolute spectral irradiance distribution being a distribution of absolute values of spectral irradiances in the area;

a photosynthetic photon flux density calculating unit that calculates a photosynthetic photon flux density based on the absolute spectral irradiance distribution; and a leaf area index calculating unit that calculates a leaf area index based on the photosynthetic photon flux density.

6. The image measuring system according to claim 5, wherein the reflector includes a perfect diffusion reflection surface whose color is known.

7. The image measuring system according to claim 5, further comprising:

a storage device that stores the photosynthetic photon flux density and the leaf area index in association with each other, wherein the leaf area index calculating unit calculates the leaf area index by extracting the leaf area index associated with the calculated photosynthetic photon flux density from the storage device storing the leaf area index.

8. The image measuring system according to claim 5, wherein the absolute spectral irradiance distribution calculating unit is operative to:

calculate a tristimulus value including a luminance value in the area based on the color information;

calculate an absolute irradiance based on the luminance value, the absolute irradiance being an absolute value of an irradiance of light in the area;

calculate a chrominance in the area based on the tristimulus value;

calculate a relative spectral irradiance distribution based on the chrominance, the relative spectral irradiance distribution being a relative distribution of spectral irradiances in the area; and calculate an absolute spectral irradiance distribution based on the absolute irradiance and the relative spectral irradiance distribution.

9. An image measuring device which uses in an image measuring system provided with a reflector arranged in vicinity of a plant to be measured, and an image capturing device that photographs the reflector and outputs a photographed image of the reflector, the image measuring device comprises:

a processor; and memory storing executable instructions that, when executed by the processor, causes the processor to perform as:

an image analysis unit that detects an area where the reflector is photographed within the photographed image and acquiring color information of the area;

an absolute spectral irradiance distribution calculating unit that calculates an absolute spectral irradiance distribution based on the color information, the absolute spectral irradiance distribution being a distribution of absolute values of spectral irradiances in the area;

a photosynthetic photon flux density calculating unit that calculates a photosynthetic photon flux density based on the absolute spectral irradiance distribution; and a leaf area index calculating unit that calculates a leaf area index based on the photosynthetic photon flux density.

10. A non-transitory computer readable recording medium that stores a computer program to use in an image measuring system provided with a reflector arranged in vicinity of a plant to be measured, and a photographing unit that photographs the reflector and outputting a photographed image of the reflector, the program causing a computer to execute:

an image analysis processing of detecting an area where the reflector is photographed within the photographed image and acquiring color information of the area;

an absolute spectral irradiance distribution calculation processing of calculating an absolute spectral irradiance distribution based on the color information, the absolute spectral irradiance distribution being a distribution of absolute values of spectral irradiances in the area;

a photosynthetic photon flux density calculation processing of calculating a photosynthetic photon flux density based on the absolute spectral irradiance distribution; and a leaf area index calculation processing of calculating a leaf area index based on the photosynthetic photon flux density.

* * * * *